United States Patent
Bagraev et al.

(10) Patent No.: US 6,171,331 B1
(45) Date of Patent: Jan. 9, 2001

(54) METHOD OF TREATING OF PATHOLOGICAL TISSUES AND DEVICE TO EFFECT THE SAME

(76) Inventors: Nikolai T. Bagraev, st. Butlerova h. 13, f. 389, 195256, St. Petersburg; Leonid E. Kliatchkin, st. Chaikovskogo h. 31, f. 20, 191194, St. Petersburg, both of (RU)

(*) Notice: Under 35 U.S.C. 154(b), the term of this patent shall be extended for 0 days.

(21) Appl. No.: 09/170,546

(22) Filed: Oct. 13, 1998

Related U.S. Application Data (63) Continuation of application No. PCT/RU96/00085, filed on Apr. 11, 1996.

(51) Int. Cl.$^7$ ................................................ A61N 21/00
(52) U.S. Cl. ................................... 607/88; 606/2; 606/9
(58) Field of Search ........................... 606/2, 3, 9–11, 606/13; 607/89–92

(56) References Cited

U.S. PATENT DOCUMENTS

| | | |
|---|---|---|
| 5,161,526 | 11/1992 | Hellwing et al. |
| 5,259,380 | 11/1993 | Mendes et al. |
| 5,282,842 | 2/1994 | Changaris . |
| 5,304,167 | 4/1994 | Freiberg . |
| 5,320,618 | 6/1994 | Gustafsson . |
| 5,358,503 * | 10/1994 | Bertwell et al. ................ 606/27 |
| 5,944,748 * | 8/1999 | Mager et al. .................... 607/88 |
| 5,957,960 * | 9/1999 | Chen et al. ...................... 607/92 |

FOREIGN PATENT DOCUMENTS

| | | |
|---|---|---|
| 4113803 | 10/1992 | (DE) . |
| 4112275 | 11/1992 | (DE) . |
| 4129192 | 3/1993 | (DE) . |
| 4707945 | 11/1991 | (RU) . |
| 2014854 | 6/1994 | (RU) . |
| 2018329 | 8/1994 | (RU) . |
| 2032432 | 4/1995 | (RU) . |
| 2033823 | 4/1995 | (RU) . |
| 2034318 | 4/1995 | (RU) . |
| 93003767 | 7/1995 | (RU) . |
| 2043759 | 9/1995 | (RU) . |
| 93015098 | 9/1995 | (RU) . |
| 2045969 | 10/1995 | (RU) . |
| 2049500 | 12/1995 | (RU) . |
| 94019587 | 12/1997 | (RU) . |
| 1781659 | 12/1992 | (SU) . |
| 1810868 | 4/1993 | (SU) . |
| 93 21842 | 11/1993 | (WO) . |

OTHER PUBLICATIONS

N. T. Bagraev et al., "Induced IR Emission in Silicon with Heavily Doped Diffused Quantum–well profiles," *American Institute of Physics*, 1993.

* cited by examiner

*Primary Examiner*—Linda C. M. Dvorak
*Assistant Examiner*—Roy Gibson
(74) *Attorney, Agent, or Firm*—Price, Heneveld, Cooper, DeWitt & Litton (57) ABSTRACT

The disclosed device is used to treat pathological tissues with a noncoherent emission. The device includes an emitter precalibrated to provide a required emission power density. The emitter includes a broad band semiconductor silicon LED including a supershallow "p–n" transition for emitting noncoherent IR emission having wavelengths ranging from 1 to 56 $\mu$m and including wavelengths at least between 26 and 56 $\mu$m. The device further includes a power supply connected along a plane of "p+n" or "n+p" transition to provide electric current inside the "p+n" or "n+p" transition region. Additionally, the device includes a control system including a plurality of leads for additional sources of electric fields that are connected to the broad band semiconductor silicon LED in such a way that an electric field is applied along the plane of "p+n" transition providing the reverse and direct shift at the "p+n" transition. The control system controls the spectrum range of the emitted light wavelength, the degree of its linear polarization, and the frequency of time modulation.

15 Claims, 9 Drawing Sheets

METHOD OF TREATING OF PATHOLOGICAL TISSUES AND DEVICE TO EFFECT THE SAME

CROSS-REFERENCE TO RELATED APPLICATIONS

This application is a continuation under 35 U.S.C. §120 of International PCT Application No. PCT/RU96/00085, filed on Apr. 11, 1996, the disclosure of which is incorporated by reference herein.

BACKGROUND OF THE INVENTION

1. Field of the Invention

The present invention generally relates to a device used for medical treatments. More particularly, the present invention is related to a device and medical treatments for treating diseases accompanied by a metabolic disorder, weakening of enzymatic processes, and a regenerative function disorder in affected tissues. The method of medical treatment is used for therapy of rheumatoid arthritis, angiopathic syndrome at diabetes mellitus, gastric and duodenal ulcers, paradontosis and paradontitis, burns, as well as during remission after local facial plastic surgery. It can also be applied for treating other diseases of the same class.

2. Description of the Related Art

A method of treating diabetic angiopathy of inferior limbs (Russian Patent No. C1, 2049500, Dec. 10, 1995) is known that implies an internal irradiation of blood with a low-frequency IR emission. A method of treating diabetes mellitus (Russian Patent No. C1 2018329, Aug. 30, 1994) is known that uses a coherent emission to directly irradiate the liquid blood component. The above methods imply a direct effect of an internal irradiation upon the blood. They, however, provide no possibility to affect the physiological processes in tissue cells, or their effects are mediated by a number of uncontrolled factors. Besides, a coherent IR emission used in this case features a lower degree of penetration into tissues, which makes its effect on the tissue structure less organic and, consequently, more rigid.

A device for general local body heating (German Patent No. 4113803, 1992) is known that provides a deep penetration of IR emission into a human body. Its curing effect, however, is provided by a rise of tissue temperature that leads to an enhanced necrosis and drying of tissues in the process of their healing, thus promoting a secondary inflammatory process and introducing an additional risk factor in case of vasodilatation in pathologically changed tissues.

A method of treating skin injuries (Russian Patent No. C1 2032432, Apr. 30, 1995) is known based on the effect produced by a pulsed monochromatized light beam in the red wavelength band. The beam pulse mode, however, is applied in a limited wavelength band as the treated tissues are exposed to light having the wavelength of only 0.6 to 0.69 $\mu$m at a reduced power density of 5 to 10 mW/cm$^2$. Thus, it cannot produce a curing effect for the whole class of diseases accompanied by metabolic disorders.

A multi-wavelength medical laser (U.S. Pat. No. 5,304, 167, Apr. 19, 1994) is known that generates a first beam of pulsed electromagnetic energy and a second beam of electromagnetic energy having its wavelength in a visible portion of the optical spectrum, with both of them affecting the tissues simultaneously. This reference, however, discloses that the laser's wave energy is used for surgery rather than therapy.

An apparatus for thermal stimulation (Russian Patent No. 2045969 C1, Oct. 20, 1995) is known that affects tissues by IR emission in order to stimulate tissue processes. However, the stimulation used for the purpose is thermal.

A method of stimulating biologically active points (Russian Patent No. 93003767 A, Jul. 27, 1995) is known that stimulates body processes through use of IR-range wavelengths that feature a better penetration through the skin. However, the irradiation waveband ranges from 0.8 to 3 $\mu$m with its source located over the biologically active points affecting the entire body functions, rather than over the organ that controls the course of disease, thus leaving the disease out of consideration.

A method for treating the bleeding of hemophiliacs (U.S. Pat. No. 5,161,526, Nov. 10, 1992) is known based on biostimulation of affected regions of muscles and joints with a beam of light. This method, however, is applied only to stop bleeding and to increase blood coagulability through use of wavelengths ranging from 5.0 to 1.1 $\mu$m that are not effective for curing the whole set of medical indications typical to the entire class of diseases in question.

A method of affecting biological objects (Russian Patent No. 93015098 A, Sep. 10, 1995) is known that uses modulated pulses of energy, for instance IR energy, to optimize functioning of the biological object energy system and to affect the region of a sore organ. This method, however, does not imply affecting metabolic, regenerative, and enzymatic processes in tissues by treating disorders in tissue capillary circulation, vascular circulation, flow of lymph, as well as treating deceleration of blood flow and oxidation-reduction processes that cause functional, anatomic, and morphological changes in the structure of tissues of all kinds. Besides, the produced effects provide no increase to the curing efficiency compared to the optimum curing effect for diseases caused by disorders of metabolic, regenerative and enzymatic processes in tissues.

The closest to the suggested method of treatment is a method of treating gastric and duodenal ulcers (Russian Patent No. 94019587 A, 1997), implying a 1 to 20 minute transcutaneous irradiation of the affected region of mucosa with IR emission having the power density of 50 to 300 mW/cm$^2$. However, the efficiency of this method is rather low, since the irradiation is performed through the skin site located directly over the affected region of mucosa and is unable to produce an optimum effect on metabolic, enzymatic, and regenerative processes in tissues. The emission has the wavelength from 7 to 25 $\mu$m. The given method of treatment provides a curing effect after a large number of irradiation sessions, however, complications are observed in the form of tissue necrosis and edema that decrease the efficiency of treatment by lowering the level of effects on tissues' regenerative, enzymatic, and metabolic processes. This is caused by the fact that the shallow penetration of the emission is unable to activate all the potentials of tissue structures across their entire thickness. Besides, activation and optimization of processes in tissues is also not equally effective for different types of tissues, different locations of affected tissues (deep or shallow), and different types of diseases. This increases the risk of relapses and complications, and decelerates the tissue healing process, since certain undesirable effects like necrosis, keloid cicatrices, and tissue edema have sufficient time to evolve.

A selective polarizing laser mirror (Russian Patent No. 2034318 C1, Apr. 30, 1995) is known with a multi-layer dielectric coat applied onto an optical substrate. The mirror polarizes the emission. The latter, however, is generated by another source, hence, its polarization parameters cannot be controlled by the given device.

A method of filtering optical emission (SU No. 1810868 C1, Apr. 23, 1993) is known based on a linear polarization of light. The method makes it possible to cut off a long-wave portion of the emission and to continuously vary the limiting passband frequency. However, it cannot linearly polarize a specific wavelength of the emission that varies in accordance with the task.

A device for treatment of undesired skin disfigurements (U.S. Pat. No. 5,320,618, Jun. 14, 1994) is known that emits a pulsating light beam. However, the light wavelength transformer used in the device does not respond to wavelength variations and cannot provide an optimum curing effect by combining a specific wavelength of the emission with a certain magnitude of its pulsation.

High energy light emitting diodes (LEDs) for photodynamic therapy (PCT Patent No. 93/21842 A1, 1993) are known. The device and the method suggested for activating the healing processes by photodynamic therapy utilize the emission of powerful LEDs in a certain preselected portion of the optical spectrum. However, a complex feedback circuit needed to monitor the light parameters makes it impossible to adjust the device to a specific type of disease.

A polarizing grating (SU No. 1781659 C1, Dec. 15, 1992) is known that polarizes light in a broad waveband from 1 to 100 $\mu$m. However, it provides for no variations of emission parameters required for treating a specific type of disease, since no wavelength selection within the preset band is envisaged. An apparatus for bioenergetic therapy (Russian Patent No. 2043759 C1, Sep. 20, 1995) is known consisting of a pulse generator and an IR generator. However, it cannot provide the required combinations of a specific wavelength of the emission with certain pulse parameters through a direct control over the light emitter to obtain an optimum curing effect for a specific disease.

An irradiating device (German Patent No. 4129192 A1, March 1993) is known that passes the varying portion of the emission through by means of a frequency-selective partially transparent glass. In other words, a spectrum, initially containing parasitic (harmful) components, is emitted and then corrected by a special unit.

An irradiating device (German Patent No. 4112275 A1, 1992) is known in which the spectrum is divided by special spectrum dividers with a dichroic coat. The device permits to emit a spectrum with preset characteristics, though provides no spectrum variation in combination with and depending upon the length, polarization, and modulation of the wave.

A method and a device for inducing tanning by pulsed light (U.S. Pat. No. 5,282,842, Feb. 1, 1994) are known. However, the device emitter is not included into the circuit designed for varying the pulse cycles, thus the device itself cannot be adjusted to a specific type of disease.

A light therapy system (U.S. Pat. No. 5,259,380, Nov. 9, 1993) is known based on LEDs that emit a narrow-band noncoherent light with a central wavelength. The LEDs are grouped into diode banks controlled by a device that generates a difference of potentials and a unit that forms a voltage with preset characteristics. However, selection of required emission parameters is performed by the entire system, rather than through use of emitter properties.

A light therapy device (Russian Patent No. 2014854 C1, Jun. 30, 1994) is known that provides a curing effect using a periodic pulsed IR beam of controlled intensity. The emission is generated by metal halogen lamps that have a certain filling and provide control over the intensity and spectral composition of the emitted light, though being unable to provide its linear polarization and ensure an optimum combination of the wave length, modulation, and polarization required for treating a specific disease.

Light therapy devices comprising light emitters and a control system (Russian Patent No. 2014854 C1, Sep. 20, 1994; and Russian Patent No. 2033823 A1, Sep. 20, 1995) are the closest by their engineering solution to the proposed device. Their emitters are calibrated depending on the requirements to the emitted flux density, and the process of controlling the flux parameters depends on the program of therapy. However, the control over the flux parameters is secured by changing the location of the emitter relative to the pathology focus or by changing the emitters themselves, which prevents selection of an optimum combination of emission characteristics to obtain the maximum curing effect for a specific disease.

The method for treating inflammatory processes and uncomplicated ulcerations of gastric and duodenal mucosa (Russian Patent No. 4707945 A1, Nov. 26, 1991) is the closest by its technical essence to the suggested method of treating pathological tissues. It envisages a possibility of simultaneous treatment of both the surface layers of mucosa and deeper layers of the organ walls with a partial absorption of the irradiation by the tissues located between these layers. However, the applied spectral band can be varied only by combining the powers supplied to the emitter, for instance to a set of halogen lamps, or by changing the distance from the distal end of an endoscope to the irradiated tissue surface. The method does not allow combining polarization and modulation together with power and wavelength variation to obtain an optimum combination of emission parameters for treating a specific disease.

SUMMARY OF THE INVENTION

A need exists for increasing the efficiency of treatment of various pathologies in several types of tissues (muscle, joint, vascular), featuring the following disorders:

metabolic disorders, specifically in the rate of extraction of microelements from the blood circulating in tissues, reduction of absorption and release of oxygen and glucose-containing elements by the blood observed at angiopathic syndrome at diabetes mellitus;

metabolic disorders in a joint cartilage at rheumatoid arthritis;

weakening of enzymatic processes and a rise in the level of metabolism at angiopathic syndrome, burns, paradontosis and paradontitis, gastric and duodenal ulcers; and disorders in the regenerative function of affected tissues, for instance at gastric and duodenal ulcers, tissue healing during remission after local facial plastic surgery, etc.

These disorders are accompanied by inflammatory processes, tissue edema, and necrosis. All the above processes occur due to a number of major reasons:

capillary circulation disorders;

vascular circulation disorders;

lymph flow disorders;

blood stream deceleration; and deceleration of oxidation and reduction processes.

In the course of listed diseases, the above-mentioned processes entail functional, anatomical, and morphological changes in the structure elements of all kinds of tissues.

These processes are characterized by changes in regional blood circulation assessed by the following parameters:

blood flow level;

pulse blood volume;

vessel wall resistance;

vascular tension;

rheographic index;

index of peripheral resistance of vessels;

tissue elasticity;

skin temperature; and pain syndrome stopping and tissue healing time.

The present invention increased the curing effect by irradiating an affected region with a noncoherent IR emission of an extended wavelength band from 1 to 56 µm while polarizing and modulating the emitted flux in combinations that produce the optimum curing effect for a specific disease caused by the above-mentioned disorders. The exposure to the noncoherent IR emission must produce an effective action upon the organ that controls the course of the disease while simultaneously affecting the whole mass of tissues (both surface and deep layers), meanwhile envisaging a possibility to optimally combine the effects of polarization and modulation of the emitted flux of a preset energy distribution. The optimum curing and the maximum therapeutic effects for a specific disease are obtained by activating various processes in tissues through use of an emission with an optimum combination of wavelengths and power densities.

The above-mentioned useful result is provided by the proposed method of treating the pathological tissues with a noncoherent emission consisting of a periodic IR irradiation of the tissues during 1 to 20 minutes at the emission power density of 50 to 300 mW/cm². The irradiation is repeated, traditionally, in one or two days depending on the time needed to stop the pain syndrome in the process of healing of pathological tissues.

The inventive method achieves advantageous results by exposing the skin site located directly above the organ controlling the course of a disease caused by metabolic, enzymatic, and regenerative disorders to IR emission of 1 to 56 µm waveband. The method may further use emission that is also linearly polarized and/or time modulated. The method may thus use a package of different wavelengths in a preset range, with a linear polarization and time modulation applied to specific wavelengths depending on the nature of the disease. The emission power density is also selected depending on the disease.

The curing effect is produced by activating metabolic, enzymatic, and regenerative processes in tissues. All the curing effects result from enhancing the blood circulation and accelerating the regenerative processes in tissues.

The present method of treatment implies a functional action of all the wave spectrum at an optimum combination of emission parameters for a specific type of disease. In all cases the activation occurs across the whole mass of affected tissues as a result of acceleration of metabolic, enzymatic, and regenerative processes. A substantial improvement of medical indications at various diseases is stipulated by an optimum combination of emission parameters, which makes the treatment period shorter and produces the maximum curing effect.

Figure 8:
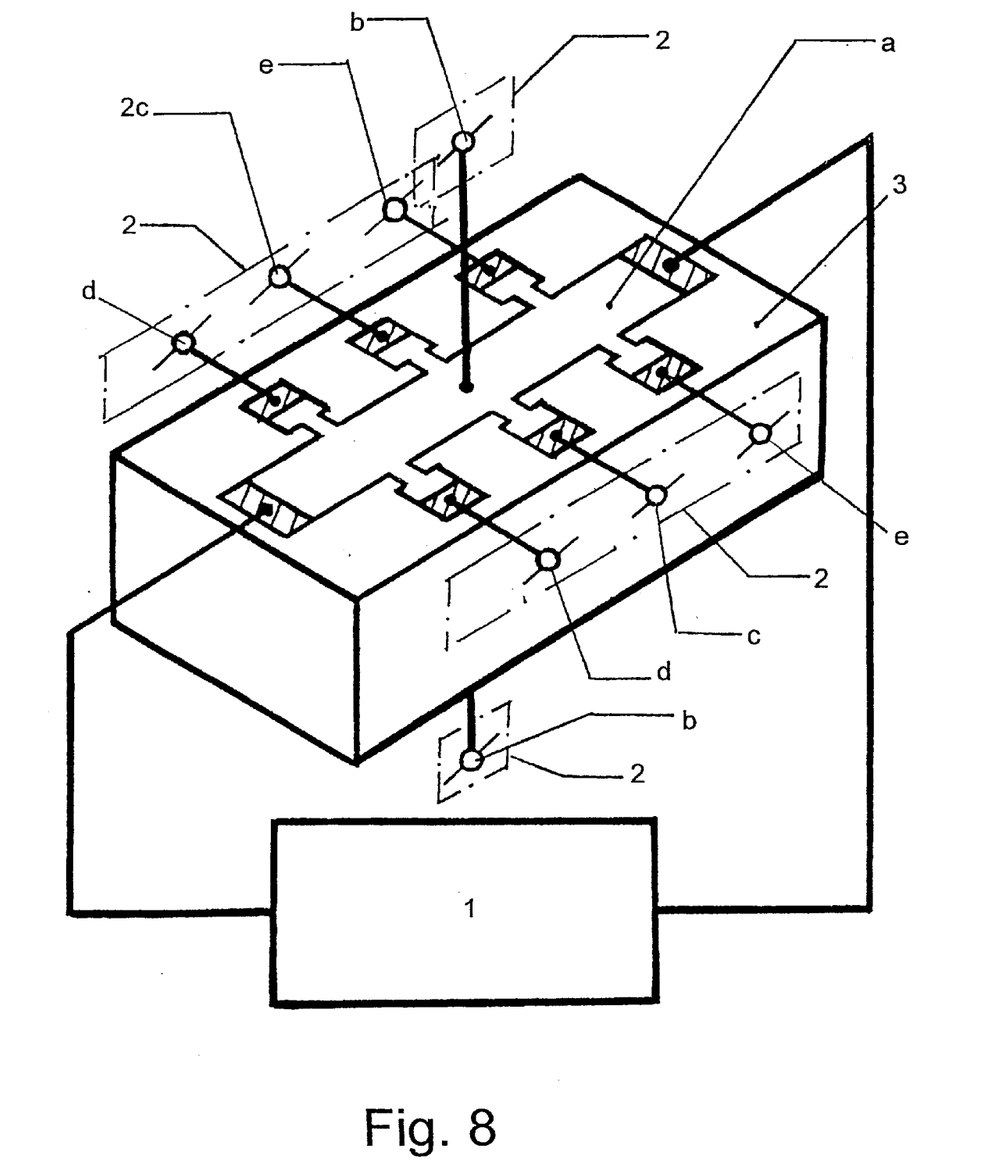
FIG. 8 is a perspective view of the device for treating pathological tissues with noncoherent emission.

The present device designed for treating pathological tissues with a noncoherent emission offers a solution to the problem of optimizing the curing effect for a specific disease. The device includes a power supply (1), an emission source comprising a control system (2), and an emitter (3). When an electric control signal is fed from additional power supplies of the control system, the inventive device provides such parameters of the emission that meet the requirements of the maximum curing effect. The emission source is precalibrated to provide the required emission power density.

The emitter of the inventive device is preferably a broad band semiconductor silicon LED based on a supershallow "p–n" transition with the wavelengths of noncoherent IR emission ranging from 1 to 56 µm and including wavelengths at least in the 26 to 56 µm range. The power supply (1) is connected along the plane (a) of "p+n" or "n+p" transition to provide electric current inside the doped "p+n" or "n+p" region. The control system (2) is equipped with leads (c, d, e) for additional sources of electric field that are connected to the LED in such a way that the electric field acts along the plane (a) of "p+n" transition providing the reverse and direct shift at the "p+n" transition. The control system (2) controls the spectrum band of the emission wavelengths, the degree of linear polarization, and the frequency of time modulation. The control system (2) controls the LED by an electric field fed from additional power supplies through leads (c, d, and e). The value of the electric field is selected depending on the nature of the disease.

To obtain the desired results, the device uses the effect of cutting out a certain wavelength band in a broad band diode by means of voltage applied to the "p–n" transition. When the controlling electric field of a preset value is fed, the emitted light is linearly polarized. The other additional controlling electric field provides modulation of the emitted light with a required frequency.

Thus, the device produces the required combination of emitted light characteristics, namely, a package of wavelengths in the preset range, presence or absence of linear polarization, and modulation of the emission with a preset frequency, for instance 200 or 30 Hz. The above optimizes the curing effect depending on the nature of the disease.

Thus, the proposed device realizes the above-mentioned method of treatment and produces an optimum curing effect depending on the nature of the disease. Consequently, the present invention makes it possible to obtain the maximum therapeutic effect depending on the nature of the disease.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 2 is a series of graphs comparing characteristics of the results of paradontosis and paradontitis treatment by emission with A1, A, B, C, D characteristics:

Variant I—values of rheographic indices (RI),

Variant II—values of indices of peripheral vascular resistance (IRP), and

Variant III—values of indices of vascular tension (IVT);

FIG. 3a is a series of graphs comparing characteristics of the results of uncomplicated gastric and duodenal ulcer treatment by emission with A1, A, B, C, D characteristics:

Variant I—number of the irradiation session at which the pain syndrome was stopped (Nc-H), and Variant II—number of the irradiation session at which the ulcer was arrested (Nk-H);

FIG. 3b is a series of graphs comparing characteristics of the results of chronic gastric and duodenal ulcer treatment by emission with A1, A, B, C, D characteristics:

Variant I—number of the irradiation session at which the pain syndrome was stopped (Nc-X), and Variant II—number of the irradiation session at which the ulcer was arrested (Nk-X);

FIG. 5 is a series of graphs comparing characteristics of the results of angiopathic syndrome treatment at diabetes mellitus by emission with A1, A, B, C, D characteristics:

Variant I—blood flow values in limbs (K) at the emission power density of 50 and 300 mW/cm$^2$, Variant II—index of skin temperature in the irradiated spot (ST) at the emission power density of 50 and 300 mW/cm$^2$, and Variant III—index of skin temperature on feet (FT) at the emission power density of 50 and 300 mW/cm$^2$;

FIG. 6 is a series of graphs comparing characteristics of treatment results after facial local plastic operations by emission with A1, A, B, C, D characteristics:

Variant I—values of pulse blood volume (PB),

Variant II—values of vascular wall resistance (VWR), and

Variant III—values of index of vascular tension (IVT);

FIG. 7 is a series of graphs comparing characteristics of the results of burn treatment by emission with A1, A, B, C, D characteristics:

Variant I—values of rheographic index (RI),

Variant II—values of index of vascular tension (IVT), and

Variant III—values of index of peripheral vascular resistance (IRP); and

DETAILED DESCRIPTION OF THE PREFERRED EMBODIMENT

Figure 1:
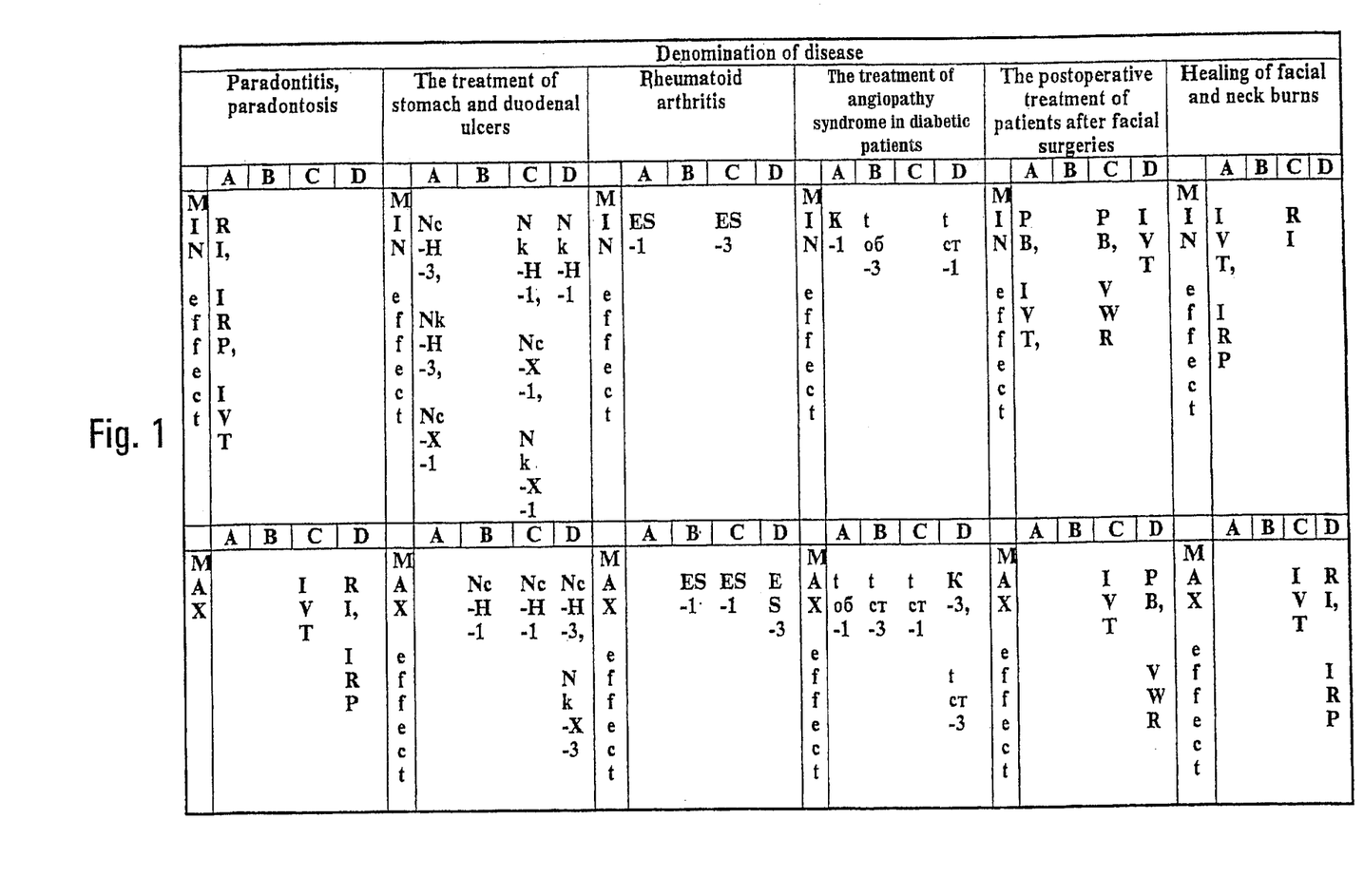
FIG. 1 is a table of the maximum and minimum curing effects depending on the type of emission and medical indication for a specific type of disease.
Figure 3A:
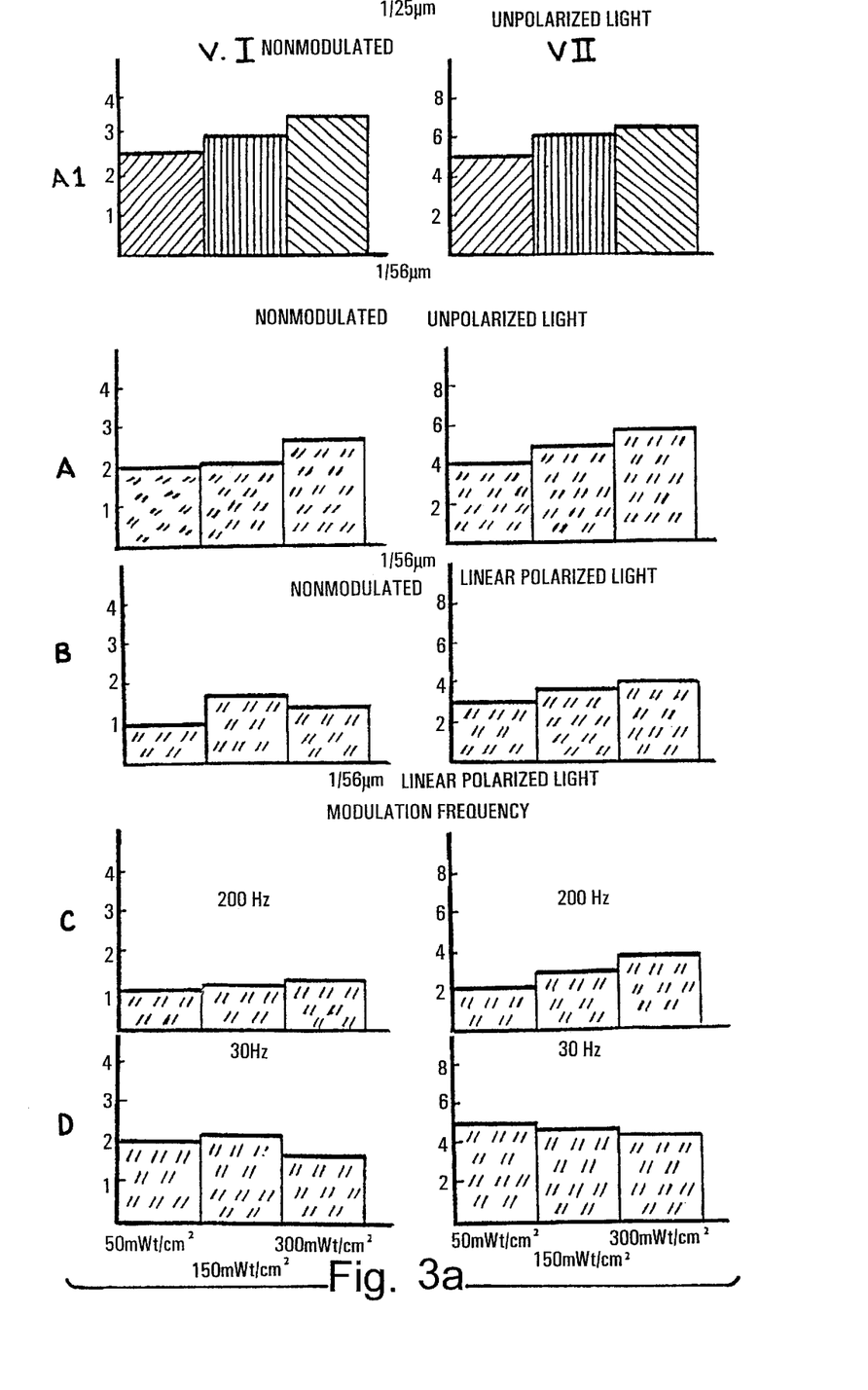
Figure 3B:
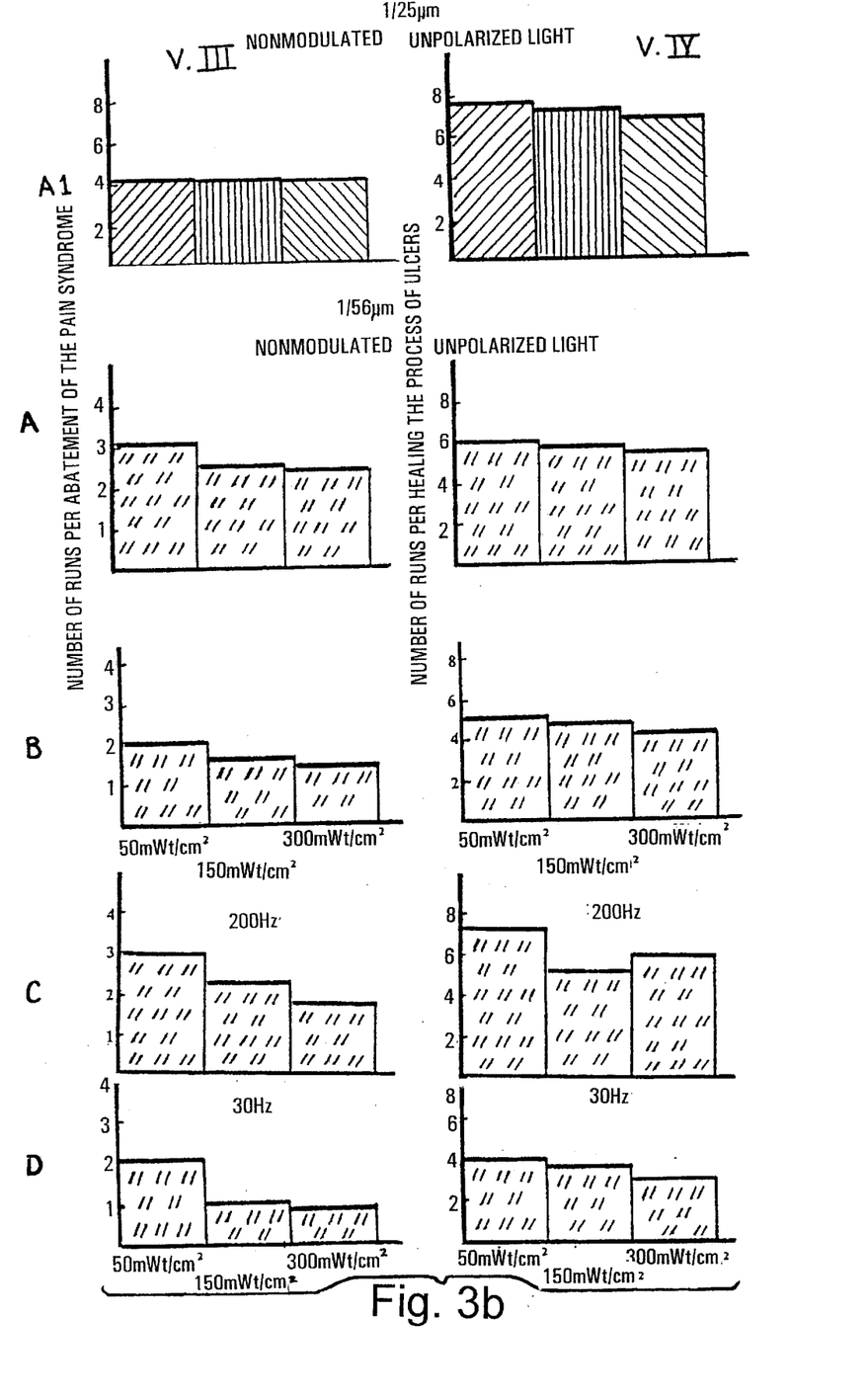
Figure 4:
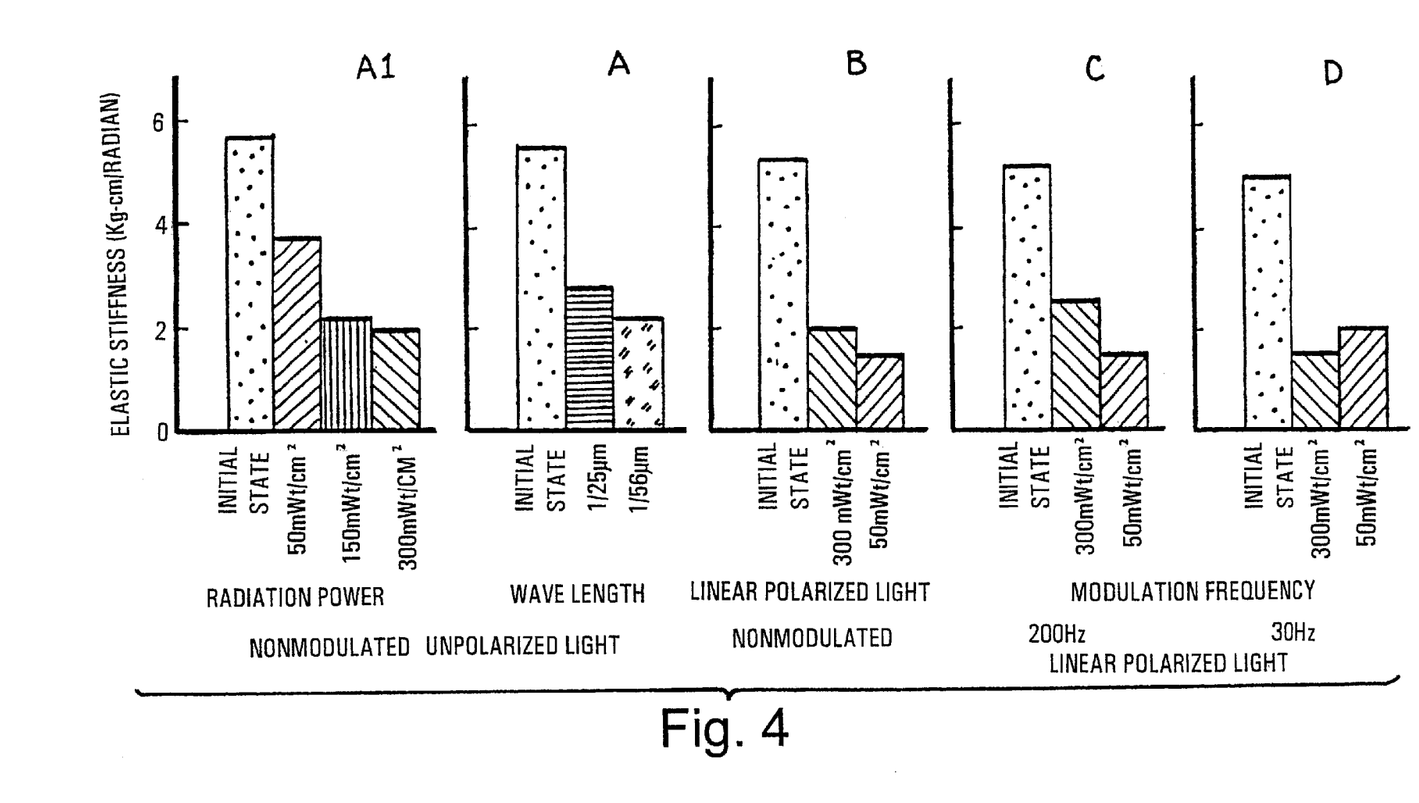
FIG. 4 is a series of graphs comparing characteristics of the results of rheumatoid arthritis treatment by emission with A1, A, B, C, D characteristics with the variant being values of indices of joint extension elasticity and flexion elasticity.
Figure 5:
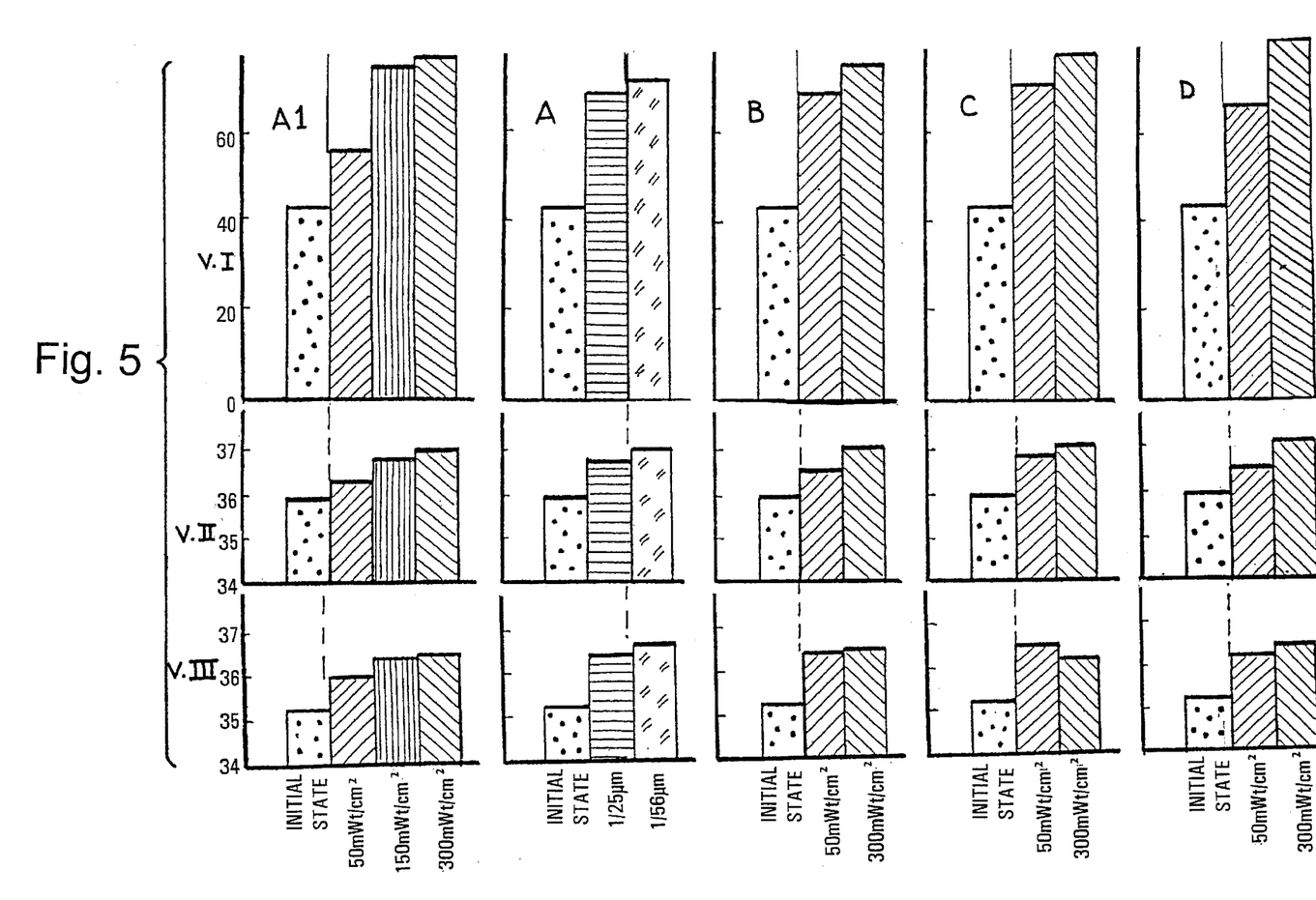
Figure 6:
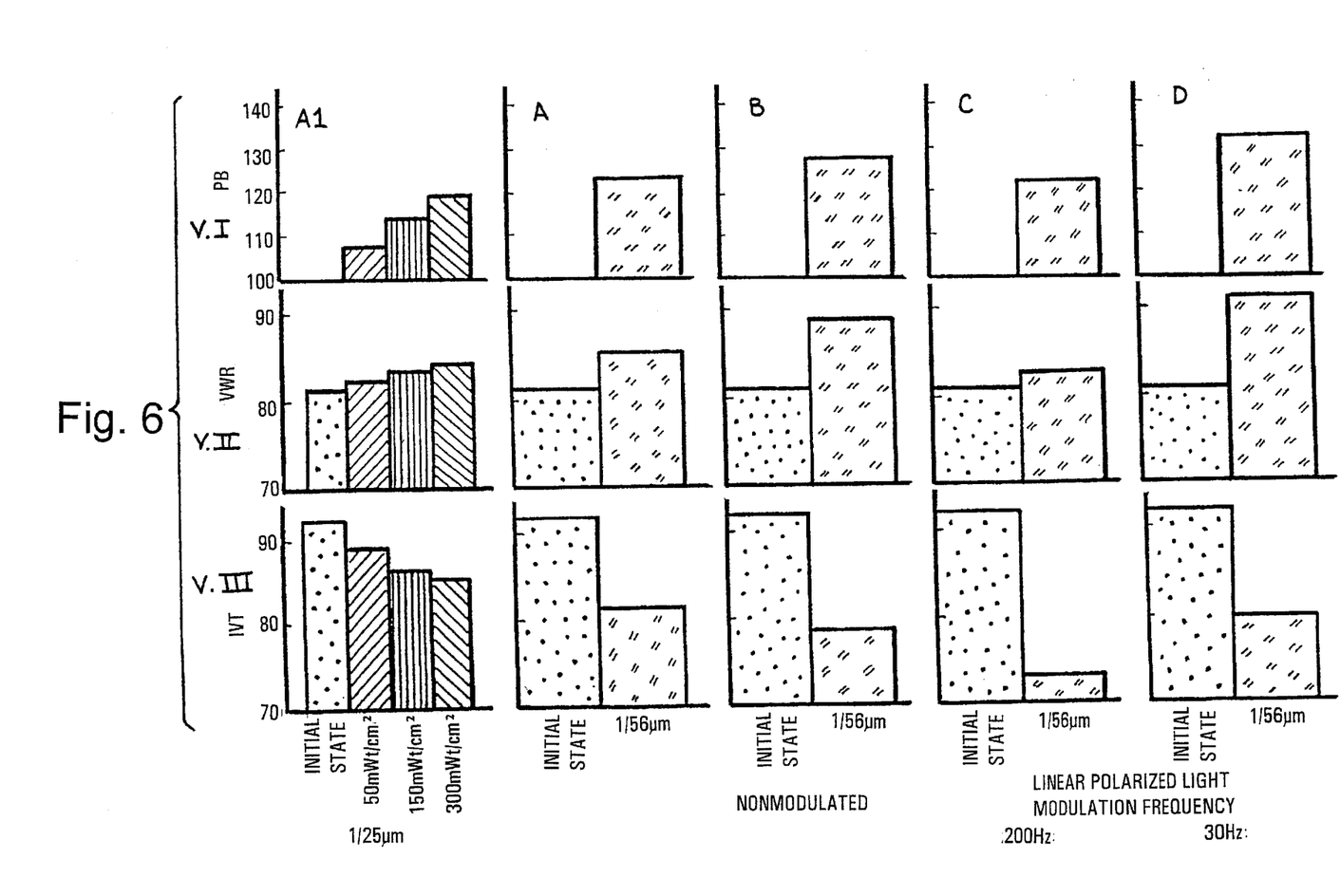
Figure 7:
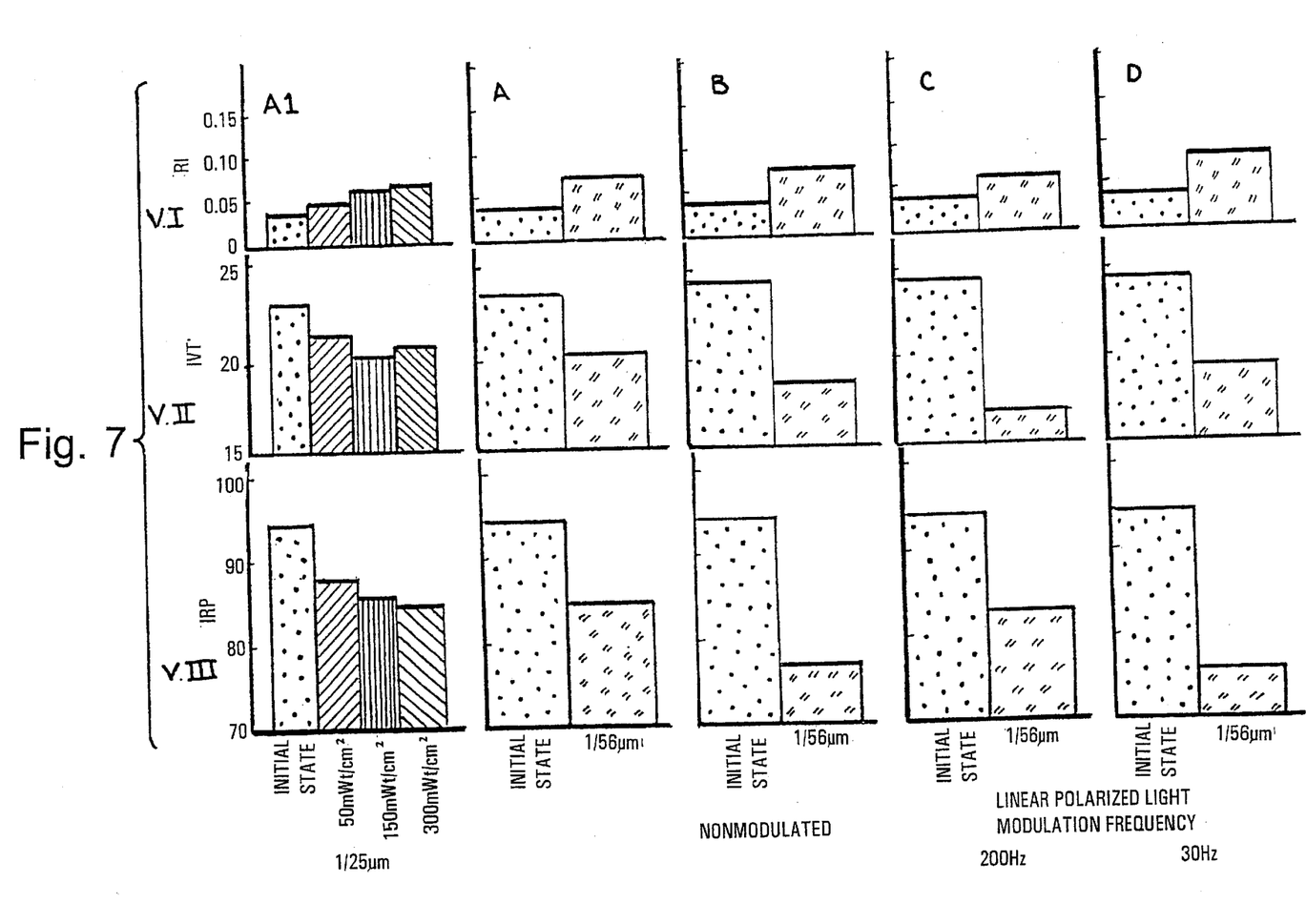

The diseases caused by metabolic, enzymatic, and regenerative process disorders result in functional, anatomical, and morphological changes in the structural elements of tissues that lead to pathologies in these tissues. Treatment of the following pathologies is considered below:

paradontitis and paradontosis cause the following pathological changes in tissues: necrosis, capillary circulation disorder in muscular tissues of gingivae, edema, inflammatory process in tissues. The gingivae feature stomatorrhagia, hyperesthesia, an increased index of hygiene (IH), rheographic index (RI), index of vascular peripheral resistance (IPR), and index of vascular tension (IVT). An emission with a package of wavelengths ranging from 1 to 56 μm combined with polarization and 30 or 200 Hz modulation produces the maximum curing effect (see FIGS. 1 and 2). The effect is characterized by stable RI-v.I, IPR-v.II and IVT-v.III (see FIG. 2), the values of which are nearing the norm. Even at the minimum curing effect produced by a nonpolarized and unmodulated 1 to 56 μm emission, the values of RI, IPR and IVT are still nearer to the norm than those produced by emission with the wavelength of 7 through 25 μm (see FIG. 2, A1). The effect results from stimulation of the blood circulation and enrichment of the blood with oxygen;

gastric and duodenal ulcers cause the following pathological changes in tissues: inflammation of mucosa, formation of keloid cicatrices as a result of ulcer healing, drying of the epithelium leading to necrosis of mucosa tissue, and a secondary inflammation resulting from an unfavorable combination of applied emission parameters that slows healing of tissues. Thus, for instance, the mucosa surface epithelium heals better after having been irradiated for a short time by emission with a higher frequency modulation (200 Hz) but without increasing the power density (see FIGS. 1, 3a, and 3b). The epithelium in the inner mucosa layers heals more effectively when irradiated for a longer period of time at an increased power of the light flux. Such treatment is characterized by a deep penetration of energy into the mucosa tissue (see FIGS. 1, 3a, and 3b), a high level of emission absorption by tissues and a better energy distribution across the tissues. The efficiency of the process is estimated by the number of irradiation sessions needed to stop the pain syndrome and to arrest the ulcer. The maximum curing effect for an uncomplicated ulcer was observed when it was irradiated by the emission with the waveband of 1 to 56 μm combined with polarization (see FIG. 3a, v.I, v.IIB) at 50 mW/cm$^2$ emission power density and the emission with the waveband of 1 to 56 μm combined with polarization and modulation at 200 Hz frequency (see FIG. 1, v.I, v.IIC and FIG. 3a). The maximum curing effect for a chronic ulcer was observed when it was irradiated by the emission with the waveband of 1 to 56 μm combined with polarization and modulation at 30 Hz frequency. Judging by the above indications, in all cases the minimum curing effect featured better results than the ones produced by emission of 7 to 25 μm, requiring 3 or 4 irradiation sessions less to stop the pain syndrome and arrest the ulcer. The curing effect is enhanced by an optimal distribution of energy across the epithelium tissue that prevents overheating of the tissue during irradiation;

rheumatoid arthritis causes local, primarily venous, circulation disorder, hypoxia of joint elements, metabolic disorder in the joint cartilage, aseptic necrosis of the joint head, and idiopathic aseptic necrosis. The state of the joint is characterized by: a) its extension elasticity in the extreme extended position (B), in the natural joint position (E), in the position corresponding to a zero degree angle after extension (C), and b) its flexion elasticity in the extreme flexed position (A), in the natural joint position (F), in the position corresponding to a zero degree angle after flexion (D). The maximum curing effect is characterized by the minimum residual effort at flexion and extension, and the maximum flexion and extension angle (FIG. 1). The maximum curing effect is produced by irradiating the joint with the emission of 1 to 56 μm waveband combined with polarization and modulation at both 200 and 30 Hz frequency, having the minimum power density of 50 mW/cm$^2$. The minimum curing effect stops the pain syndrome and normalizes the partial capillary pressure 3 to 4 irradiation sessions earlier than it occurs at irradiation by emission of 7 to 25 μm (FIG. 4, A1);

angiopathic syndrome at diabetes mellitus causes a decrease of microelements stabilization in tissues, deterioration of absorption of oxygen and oxygen-containing elements by the blood, and deterioration of hormone production as well as metabolic functions. The localization and suppression of these effects by irradiation are characterized by a rise of skin temperature in the irradiated spot and on feet depending on the change in cell membrane penetrability that affects the energy exchange between the cells, their enzymatic and regenerative activity, and hormone production. The maximum curing effect is produced by the emission of 1 to 56 μm waveband, which is either polarized at power density of 50 mW/cm$^2$ or modulated at power density of 300 mW/cm$^2$ (FIGS. 1 and 5). The minimum curing effect produced the results that surpassed the efficiency of treatment with the emission of 1 to 25 μm waveband (FIG. 5, A1). The results were confirmed by a drop of temperature to almost normal value and by questioning patients that testified to the fact that the pain in muscles and joints, the muscle tension, and the restriction of movement were decreasing much faster. The produced effect is caused by intensification of blood circulation. This indicates a pronounced stimulation of the tissue exchange level, peroxide oxidation in particular, since, prior to the treatment, the blood circulation volume per minute was correlated with the level of glucose and immunoreactive insulin in the blood.

the remission period after local facial plastic operations causes the following highly undesirable pathological changes: mechanical injuries to tissues inflicted by surgery, aseptic inflammation of tissues, edema of soft tissues, and formation of keloid cicatrices of connective tissue. These changes are assessed by the degree of changes in the regional circulation manifested by a decrease of pulse blood volume (PB) and vascular wall resistance (VWR) that serve as indices of blood microcirculation. The changes are also characterized by a lower index of vascular tension (IVT) and presence or absence of edema. The maximum curing effect is produced by an emission of 1 to 56 μm waveband combined with polarization and modulation at 200 or 30 Hz frequency depending on the specific indication (FIG. 1 and FIG. 6C, D). The minimum curing effect brings the above indications nearer to the norm than when the patient is treated with the emission of 1 to 25 μm waveband (FIG. 6, A1) because of better microcirculation and skin cell regeneration. A positive treatment dynamics was observed, with the pain and edema decreased as a result of only one irradiation session. After the whole course of treatment the wounds healed by first intention without suppuration or suture separation;

burns cause inflammation processes in wounds, vascular disorders due to trichangiectasia and deceleration of blood circulation, edemas and hypertrophied granulation of tissues, necrosis. These processes are characterized by a rise in the rheographic index (RI), the index of vascular tension (IVT), and the index of vascular peripheral resistance (IRP). The maximum curing effect is produced by the emission of 1 to 56 μm waveband combined with polarization and modulation at 200 or 30 Hz frequency depending on the specific indication (FIGS. 1 and 7). The minimum curing effect yields the results that are nearer to the norm than those produced by the emission of 1 to 25 μm waveband (FIG. 7, A1). A visual observation showed a faster healing of wounds and resolution of edemas, as well as a smaller size of boundary cicatricial deformation of the transplanted graft of skin tissue.

The proposed method of treatment was tested on groups of 60 patients each. The groups were formed by the age criterion. The control groups consisted of either primary uncomplicated or chronic patients divided into subgroups by age (from 17 to 68 years) irrespective of sex. All the control parameters were measured during remission or when the pain syndrome was stopped. The organ responsible for the course of the disease was irradiated for a period of 20 minutes in 1 or 2 days depending on the patient's state. The measurements were made after 10 irradiation sessions. In case the pain syndrome was stopped or the ulcer arrested, the number of sessions needed to reach the effect was registered. The treating emission was directed at the spot of the skin located directly above the organ or the joint responsible for the course of the disease. The surface area of the light spot was selected such as to provide the three control values of power density, i.e., 50, 150 and 300 mW/cm$^2$. The control measurements were performed prior to and after the treatment. The patients of the control group were irradiated with the emission of 7 to 25 μm waveband, and the same parameters that characterize the treatment efficiency were registered.

To select a proper distance between the LED and the surface of the organ responsible for the course of the disease, the light source of the emitter was calibrated. This is caused by a different degree of IR absorption that depends on the combination of specific wavelengths within the band of 1 to 56 μm.

The semiconductor LEDs emit in the far IR spectrum by forming correlation gaps in the density of states of the electron or degenerate hole gas generated in heavily doped quantum-size doping profiles (publications on the subject are known, for instance: N. T. Bagraev, L. E. Klyachkin, E. I. Chaikina: IR-emission Induced in Silicon by Heavily Doped Quantum-Size Diffusion Profiles. *Sov. Phys JETP Lett.*, 58, (1993) 598). The degree of disorder in the size of correlation gaps and its distribution inside the doped region of the "p–n" transition controls the characteristics of the emission.

The device provided different combinations of the emission characteristics. All the medical control measurements were performed after irradiation. The emission parameter combinations for all groups of patients were taken the same. They were as follows:

A1—emission of 7–25 μm waveband;
A—emission of 1–56 μm waveband;
B—emission of 1–56 μm waveband combined with linear polarization;
C—emission of 1–56 μm waveband combined with linear polarization and modulation at 200 Hz;
D—emission of 1–56 μm waveband combined with linear polarization and modulation at 30 Hz.

The method of treatment of pathological tissues with a noncoherent emission can be applied as follows:

EXAMPLE 1

Figure 2:
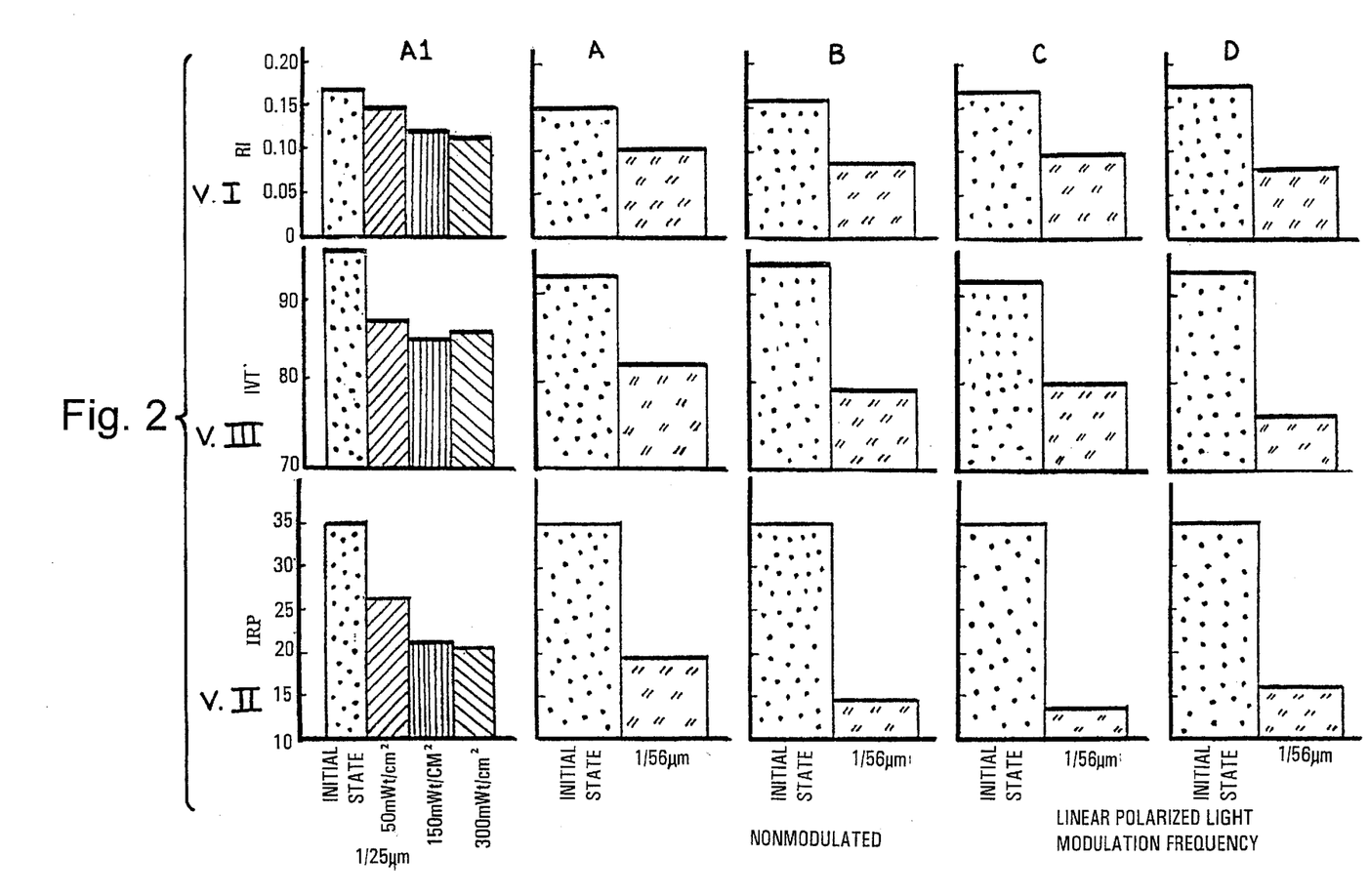

A group of patients aged from 30 to 57 years with diagnosed paradontitis or paradontosis was irradiated with the emission of 1–56 μm waveband combined with linear polarization and modulation at 200 and 30 Hz. After 5 irradiation sessions all the medical indications typical for this disease were normalized, with deviation from the norm being not more than 1 percent, the gingivae edema and bleeding were resolved. The treatment was monitored both visually and by rheographic measurements as shown in FIG. 2.

EXAMPLE 2

A group of patients aged from 27 to 66 years with diagnosed gastric and duodenal ulcer was irradiated with an emission of 1–56 μm waveband combined with linear polarization and modulation at 200 and 30 Hz. After 3 irradiation sessions a normalization of the main medical indications was observed. The pain syndrome was stopped after the first session, while the ulcer was arrested after 3 to 5 sessions. No secondary inflammation processes or tissue edema occurred. The treatment was monitored using a transendoscopic method and by questioning the patients (see FIGS. 3a and 3b).

EXAMPLE 3

A group of patients aged from 35 to 68 years with diagnosed rheumatoid arthritis was irradiated with an emission of 1–56 μm waveband combined with linear polarization and modulation at 200 and 30 Hz. After 10 irradiation sessions the elasticity of joint tissues and the level of internal friction in joints were restored up to the norm, the pain syndrome was stopped, and the partial capillary pressure was restored. The treatment was monitored using a method of transcutaneous polarography and dynamic diagnosis (see FIG. 4).

EXAMPLE 4

A group of patients aged from 17 to 53 years with diagnosed angiopathic syndrome at diabetes mellitus was irradiated with an emission of 1–56 μm waveband combined with linear polarization and modulation at 200 and 30 Hz. After 7 irradiation sessions a substantial improvement in blood flow rate in limbs was observed with a deviation from the optimum value being not more than 2 percent. The skin temperature in the irradiated spot and on feet went down to normal. The pain in muscles and joints subsided, the muscular tension normalized, and flexibility of joints increased. The treatment was monitored by rheographic measurements with calculations made by the Tishenko method. The subjective indications were monitored by questioning the patients (see FIG. 5).

EXAMPLE 5

A group of patients aged from 18 to 48 years in the remission stage after a facial local plastic surgery was irradiated with an emission of 1–56 μm waveband combined with linear polarization and modulation at 200 and 30 Hz. After 10 irradiation sessions the medical indications of pulse blood volume, vascular wall resistance, and the index of vascular tension normalized. The edema of soft tissues was resolved. The to treatment was monitored by rheovasography of facial arteries (see FIG. 6).

EXAMPLE 6

A group of patients aged from 16 to 40 years with first and second rate burns of face and neck was irradiated with an emission of 1–56 μm waveband combined with linear polarization and modulation at 200 and 30 Hz. After 10 irradiation sessions the following medical indications normalized: the rheographic index, the index of vascular tension, and the index of vascular peripheral resistance. The skin grafts transplanted for autoplasty featured a reduction in tissue edge necrosis and hypertrophied granulation as well as in astringent keloid cicatrices development (see FIG. 7). The treatment was monitored both visually and by rheographic measurements of intact skin 1 to 3 mm away from the burnt site.

FIG. 8 shows the treatment device as constructed in accordance with the present invention. The device includes a power supply 1 and an emission source, which includes a control system 2 and a broad band semiconductor silicon LED 3 having a supershallow "p–n" transition for emitting noncoherent IR emission. Power supply 1 is connected along a plane (a) of the "p+n" or "n+p" transition to provide electric current inside the "p+n" or "n+p" transition region. The p–n transition is configured to normally emit light in the spectral range of 1–56 μm.

Control system 2 further includes a plurality of additional leads for additional sources of electric fields to be connected to broad band semiconductor silicon LED 3 in such a way that an electric field is applied along the plane of "p+n" transition providing the reverse and direct shift at the "p+n" transition. Control system 2 may thus control the spectrum range of the emitted light wavelength, the degree of its linear polarization, and the frequency of time modulation.

The method of treatment is best implemented by the following method of operating the inventive device.

Once a current-stabilized power supply (1) is connected to the device, the current starts flowing through the P+(n+) region of the emitter (3). The "p–n" transition emits light in the spectral range of 7–25 μm. A voltage from one of the additional power supplies is fed to the control system (2) through the terminal (b), thus expanding the spectral range up to 1–56 μm. The voltage fed between the terminals (c) in the "p–n" transition plane converts the non-polarized emission of "p–n" transition into a linearly polarized one with all other emission characteristics preserved. The voltage fed between the terminals (d) converts the unmodulated (continuous) emission of the "p–n" transition into a 200 Hz modulated one with all other emission characteristics preserved. The voltage fed between the terminals (e) converts the unmodulated (continuous) emission of the "p–n" transition into a 30 Hz modulated one with all other emission characteristics preserved.

Thus, the proposed device emits the emission that provides an optimum treating regimen for the whole class of diseases caused by metabolic, enzymatic, and regenerative process disorders.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the Doctrine of Equivalents.

The invention claimed is:

1. A method of treating pathological tissues:
   providing a source of noncoherent radiation in the 1 to 56 μm wavelength band and having an emission power density of 50–300 mW/cm$^2$;
   directing the noncoherent radiation at a skin site directly over the organ responsible for the course of a disease caused by metabolic, enzymatic, and regeneration process disorders in tissues;
   selectively introducing linear polarization and time modulation to the noncoherent radiation depending on the nature of the disease; and
   periodically irradiating the skin site for 1 to 20 minute intervals.

2. A method of treating pathological tissues:
   providing a source of noncoherent radiation in at least the 26 to 56 μm wavelength band and having an emission power density of 50–300 mW/cm$^2$;

directing the noncoherent radiation at a skin site directly over the organ responsible for the course of a disease caused by metabolic, enzymatic, and regeneration process disorders in tissues; and periodically irradiating the skin site for 1 to 20 minute intervals.

3. The method of claim 2, wherein said radiation is linearly polarized.

4. The method of claim 2, wherein said radiation is time modulated.

5. The method of claim 4, wherein said radiation is linearly polarized.

6. The method of claim 5, wherein the wavelengths of the radiation within the 26 to 56 μm wavelength band and introduction of linear polarization and time modulation are selected depending on the nature of the disease.

7. The method of claim 2, wherein the emission power density is selected depending on the nature of the disease.

8. The method of claim 2, wherein the radiation further includes wavelengths in the 1 to 26 μm range.

9. A device for treating pathological tissues with a noncoherent emission comprising:

a source of light emission including a broad band semiconductor silicon LED including a supershallow "p−n" transition for emitting noncoherent IR emission having wavelengths ranging from 1 to 56 μm; and a power supply connected along a plane of "p+n" or "n+p" transition of said LED to provide electric current inside the "p+n" or "n+p" transition region.

10. The device of claim 9 and further including a control system including a plurality of leads for additional sources of electric fields that are connected to said broad band semiconductor silicon LED in such a way that an electric field is applied along the plane of "p+n" transition providing the reverse and direct shift at the "p+n" transition, said control system controls the spectrum range of the emitted light wavelength, the degree of its linear polarization, and the frequency of time modulation.

11. The device of claim 10, wherein said control system controls said broad band semiconductor silicon LED by the electric fields fed from additional power supplies through said plurality of leads, with the values of said electric fields selected depending on the nature of the disease.

12. A method of using the device of claim 9 comprising the steps of:

directing the noncoherent IR emission from the device at a skin site directly over an organ responsible for the course of a disease caused by metabolic, enzymatic, and regeneration process disorders in tissues; and periodically irradiating the skin site for 1 to 20 minute intervals.

13. The device of claim 9, wherein the noncoherent IR emission includes wavelengths at least between 26 to 56 μm.

14. A device for treating pathological tissues with a noncoherent emission comprising:

a source of light including a broad band semiconductor silicon LED including a supershallow "p−n" transition for emitting noncoherent IR emission having wavelengths ranging throughout the 1 to 56 μm range; and a power supply connected along a plane of "p+n" or "n+p" transition of said LED to provide electric current inside the "p+n" or "n+p" transition region.

15. A device for treating pathological tissues with a noncoherent emission comprising:

a source of light including a broad band semiconductor silicon LED including a supershallow "p−n" transition for emitting noncoherent emission having wavelengths within a 1 to 56 μm range, wherein said source of light including means for linearly polarizing and time modulating the noncoherent emission; and a power supply connected along a plane of "p+n" or "n+p" transition of said LED to provide electric current inside the "p+n" or "n+p" transition region.

* * * * *